United States Patent [19]

Kennedy

[11] 4,080,736
[45] Mar. 28, 1978

[54] METHOD AND APPARATUS FOR FORMING A DENTAL PROSTHESIS

[75] Inventor: Leland T. Kennedy, Richmond, Va.

[73] Assignee: IPCO Hospital Supply Corporation Whaledent International Division, New York, N.Y.

[21] Appl. No.: 724,966

[22] Filed: Sep. 20, 1976

Related U.S. Application Data

[63] Continuation-in-part of Ser. No. 582,813, Jun. 2, 1975, Pat. No. 3,987,545.

[51] Int. Cl.² ............................................. A61C 13/00
[52] U.S. Cl. ............................................................ 32/2
[58] Field of Search ........................................ 32/2, 17

[56] References Cited

U.S. PATENT DOCUMENTS

| 3,431,648 | 3/1969 | Colman | 32/17 |
| 3,722,097 | 3/1973 | Kubalek | 32/17 |

*Primary Examiner*—Robert Peshock
*Attorney, Agent, or Firm*—Friedman, Goodman & Teitelbaum

[57] ABSTRACT

A method and apparatus for forming a dental prosthesis in situ for the restoration of one or more missing, worn or broken teeth. The method includes forming an elastomeric mold half containing a corrected model of tooth areas to be restored, and forming a hard model of the tooth areas after they have been prepared for restoration. A pair of channels are placed through the elastomeric mold at spaced apart locations. The elastomeric mold and the hard model are secured together to form an assembly including a mold cavity therein. The assembly is placed in a vacuum chamber which can be pumped to produce a vacuum inside the chamber and inside the mold. One of the channels of the mold is connected to an overflow container within the vacuum chamber, and the other of the channels is connected to a source of liquid prosthesis forming material which is contained outside of the vacuum chamber. The connection between the source of material and the assembly is initially closed during which the vacuum chamber is pumped out producing a vacuum therein to a predetermined level. The connection between the source and the assembly is then opened whereby the liquid prosthesis forming material is pushed into the mold cavity within the assembly.

11 Claims, 10 Drawing Figures

METHOD AND APPARATUS FOR FORMING A DENTAL PROSTHESIS

RELATIONSHIP TO OTHER APPLICATIONS

This application is a continuation-in-part application of Ser. No. 582,813, filed on June 2, 1975 and now U.S. Pat. No. 3,987,545 issued Oct. 26, 1976, for "Method and Apparatus for Making a Dental Prosthesis in Situ," by the same inventor. All the information contained in the aforereferenced application is herein incorporated by reference.

BACKGROUND OF THE INVENTION

This invention relates to an improved method and apparatus for molding a dental prosthesis in situ.

It has previously been known to form a temporary prosthesis for the restoration of defective teeth in a patient's mouth by forming the temporary prosthesis directly in the patient's mouth. Such method first requires the formation of a negative impression of the patient's mouth before preparation of the teeth to receive the prosthesis. Then, the teeth are prepared by cutting them down as necessary and attending to various undercuts, etc. A cold adhering acrylic resin mixture is formed into a dough-like consistency which is then packed into the negative impression in the area to be restored. The negative impression, now with the mass of acrylic resin, is then inserted in the patient's mouth over the prepared teeth. The acrylic resin is allowed to cure in the mouth. The negative impression is them removed leaving the cured acrylic resin over the teeth. Finally, the cured acrylic resin is also removed from the mouth, trimmed off and formed as a temporary restoration.

This method has numerous problems, mainly because of the required use of the dough-like mass of acrylic resin formed in the patient's mouth. Frequently, the material squeezes out between the impression and the mouth forming a flash around the restoration. The flash produces many problems including flowing over adjacent teeth and tissue, preventing the impression to be fully seated in the mouth, requiring further recontouring of the restoration and exerting hydraulic pressure against the contour of the flexible impression material deforming the surface of the prosthesis. Additional problems of using the dough-like acrylic resin are well known.

Because of these problems, the aforereferenced patent application provided an improved method of forming a dental prosthesis in situ in the patient's mouth. The method of the referenced patent includes the formation of an elastomeric mold half over a positive model of the patient's jaw in the area where tooth restoration is required. The mold is formed with overlapping boundaries of the tooth area to be restored in all directions by a predetermined distance. Two holes are drilled through the elastomeric mold at opposite ends of the mold cavity. Tubular fittings are applied to each of the holes and connect to flexible tubes. One of the tubes is a flexible exhaust tube having a filter therein, while the other tube is a flexible inlet tube. The patient's teeth are then prepared for the restoration including the cutting down of selected teeth. The elastomeric mold half is then placed back onto the patient's mouth over the tooth areas prepared for restoration with the free ends of the flexible tube leading outside of the mouth. The free end of the exhaust tube is connected to a vacuum pump while the free end of the inlet tube is connected to a receptacle containing a mix of self-curing liquid resin, and especially acrylic resin. With the inlet tube clamped, a predetermined vacuum is then formed in the mold cavity. The elastomeric mold is thereby sealed around the patient's mouth so that the vacuum is maintained within the mold cavity. After the vacuum is achieved, the inlet tube is opened whereupon atmospheric pressure acting on the liquid resin in the receptacle forces the liquid resin through the inlet tube into the evacuated mold cavity. The liquid resin is allowed to cure until solid and then the elastomeric mold removed.

The formation of the dental prosthesis in accordance with the aforereferenced patent application presents numerous advantages as is described therein. However, one of the problems with that method is that the prosthesis is formed directly in the patient's mouth. This requires keeping the patient still with various dental machinery attached to his mouth for long periods of time. Specifically, during all the time that the vacuum is formed, the seal is tested, and the acrylic liquid resin is flowing in and curing, the patient must remain in position with his mouth open while supporting all of the various dental machinery. This becomes quite burdensome. Additionally, since the vacuum is formed directly in the patient's mouth between the inner surface of the elastomeric mold and the outer surface of the prepared teeth, there must be provided sufficient overlapping of the elastomeric material to form the seal directly in the mouth. This requires larger elastomeric molds and more discomfort to the patient. Also, it requires that the seal be tested until a proper vacuum is supported within the mold cavity. This may mean repeated attempts until such time as a proper seal is formed between the elastomeric mold and the patient's mouth. Furthermore, the apparatus of the system includes pumps, tubing, clamps, etc. all of which must be supported adjacent the patient's mouth which makes for a complex procedure.

The solution to these problems would be to form the temporary prosthesis externally of the patient's mouth utilizing a mold cavity formed between the elastomeric mold and a stone model of the patient's teeth. However, the process of the aforereferenced application is dependent upon the forming of a seal between the two halves of the mold cavity whereby the mold cavity itself must be capable of maintaining the vacuum. In the aforereferenced application, the mold cavity is formed between the elastomeric mold half and the patient's mouth and a seal must be provided between them so that a vacuum can be maintained within the cavity.

As a result, the aforementioned process of the referenced application could not be used on a stone model of the patient's teeth because a vacuum seal could not be made between the elastomeric mold half and the stone model. As is known, a stone model is not dense enough to prevent leakage of air between the two mold halves. As a result, any attempt to maintain a seal between them and have the mold cavity formed between the elastomeric mold half and a stone model to support the vacuum would not be feasible.

A possible solution would be to form a partial vacuum in such cavity between the elastomeric mold and the stone model and maintaining such partial vacuum by continuous pumping of the vacuum pump thereby forming a continuous evacuation of the cavity. The pump would, of course, have to have sufficient capacity to pump out sufficient volume so as to overcome the air coming into the mold cavity as a result of the leakage. However, the continuous pumping necessary to evacuate such a mold cavity would be centrary to the principles of the technique of the invention. The technique is dependent upon forming a "static" vacuum i.e., where no pumping is carried out while the material is being introduced into the mold. Specifically, the static vacuum is formed by first clamping the inlet pipe while a vacuum is produced in the mold cavity. then, after the formation of the vacuum, the clamp is released whereby atmospheric pressure pushes the liquid resin into the mold cavity. Utilizing continuous pumping would pull the material into the mold cavity. The static vacuum of the invention allows the material to be pushed into the mold which provides the improved prosthesis desired.

SUMMARY OF THE PRESENT INVENTION

It is therefore an object of the present invention to provide an improved method and apparatus for making a dental prosthesis in situ without the accompanying flash.

A further object of the present invention is to provide a method and apparatus for making a dental prosthesis between an elastomeric mold half and a stone model half by utilizing atmospheric pressure to push liquid resin into the mold cavity.

Still a further object of the present invention is to provide an improved method and apparatus for making a dental prosthesis in situ which does not require the mold cavity to completely support the vacuum in order to force in the liquid resin material.

Briefly, the invention provides a method for forming a dental prosthesis in situ by forming an elastomeric mold of a corrected model of the tooth areas which are to be restored. The tooth areas to be restored are then prepared for the restoration including the removal of any portions of teeth needed. A hard model of the tooth areas prepared for restoration is then formed. A pair of channels are placed through the elastomeric mold at spaced apart locations. The elastomeric mold is then secured to the model to form an assembly including a mold cavity therein. The assembly is then placed in a vacuum chamber whereby a vacuum can be pumped inside of the chamber. An overflow container is connected inside of the vacuum chamber to one of the channels. A source of liquid prosthesis forming materials is positioned outside of the vacuum chamber and is connected to the other one of the channels. The connection between the source of material and the assembly is closed, during which time a vacuum is pumped inside of the chamber to a predetermined level. The connection is then opened to permit atmospheric pressure to act upon the liquid prosthesis forming material pushing it into the mold cavity.

The apparatus of the present invention includes an elastomeric mold half which has been prepared over a first positive model of the patient's jaw requiring restoration, the mold half having an internal impression of the restoration desired. Additionally, there is included a second positive model of the patient's jaw including the preparations made for receiving the prosthesis, a vacuum chamber, an overflow container means adapted to be connected to the elastomeric mold half and positioned within the vacuum chamber, a flexible inlet conduit means adapted to be connected between the elastomeric mold half and a source for containing a mix of self-curing liquid resin, wherein the source itself is outside of the vacuum chamber, means for securing together the elastomeric mold half and the second positive mold, and means for opening and closing the inlet tube.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DESCRIPTION OF THE PREFERRED EMBODIMENT

The invention will be described with reference to the drawings which illustrate the sequence of steps and apparatus for forming a dental prosthesis in situ.

In accordance with the method of the invention, a positive model 10 is made of the patient's jaw on which tooth restoration is required. This is done in a conventional manner by first taking a negative impression of the jaw, then pouring a mix of hard setting dental model forming material, such as dental stone, into the impression and allowing the mix to set, whereupon the impression is separated from the dental stone thus providing a positive model of the patient's existing dentition. The model is then corrected by adding wax to areas which are to be restored. Such areas include areas where there are missing teeth, broken parts of teeth, etc. The wax is shaped to the size and shape of the desired restoration and thus a model of the patient's jaw with the deficiencies of dentition corrected is obtained. For purpose of illustration, the areas of the model 10 which have been corrected include the front teeth 12 and 13 of the patient's lower jaw. The front teeth may have been knocked out, or broken as a result of an accident. In any case, the dentist has determined that a permanent bridge is required to restore the missing or broken teeth, and while the permanent bridge is being prepared, a temporary bridge will be molded in situ according to the method of the invention.

After correcting the model, a mix of a room temperature vulcanizing silicone rubber (hereafter referred to a RTV silicone rubber) of a type which is commonly used in dentistry is prepared. The mix is applied to the corrected model to form a negative impression of the area which is to be restored, or bridged. It is necessary for the RTV silicone rubber mix to be spread over the area to be restored sufficiently thick so that upon setting, the silicone rubber may be handled without tearing. After the RTV silicone rubber mix is applied as described, the model 10 (with mix applied) is placed in a pressure pot. The pot is then closed and 30 pounds per square inch of air pressure is applied while the mix of RTV silicone rubber is curing. This provides for a denser cured silicone rubber and a better adaptation of the silicone rubber to the prepared model 10 than can be obtained by letting the RTV silicone rubber core under normal room atmospheric conditions.

Figure 1:
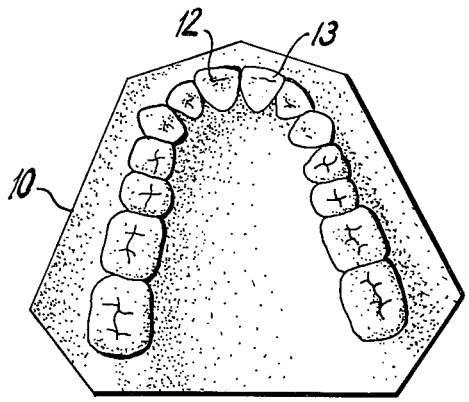
FIG. 1 is a top plan view of a corrected positive model of a patient's jaw.
Figure 2:
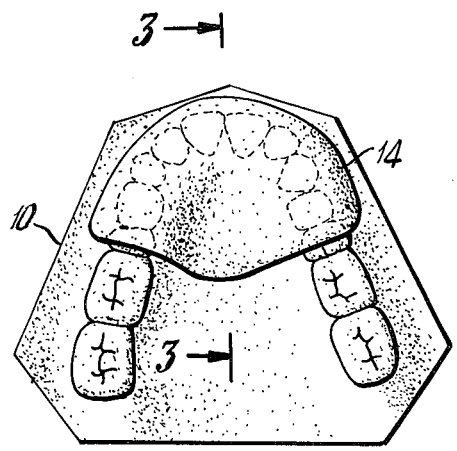
FIG. 2 is a top plan view of the model being used as a pattern with pliable mold forming material applied over the area of the jaw requiring tooth restoration to make an elastomeric mold of the patient's jaw.
Figure 3:
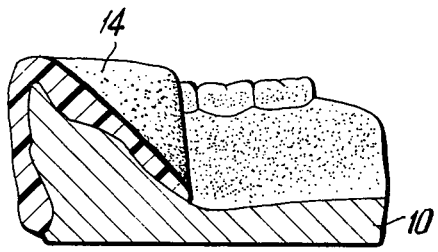
FIG. 3 is a cross sectional view taken on line 3—3 of FIG. 2.
Figure 4:
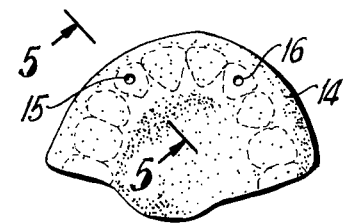
FIG. 4 is a top plan view of the elastomeric mold removed from the model with a pair of holes formed through the mold at opposite ends of the area requiring tooth restoration.
Figure 5:
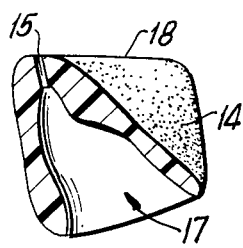
FIG. 5 is a cross sectional view taken on line 5—5 of FIG. 4.

Once the RTV silicone rubber mold 14 is cured, it is removed from the model 10, and it appears as shown in FIGS. 4 and 5. Thus, what is obtained is a negative impression of the area of the temporary bridge area (i.e. the restoration area), referred to as the elastomeric mold half. A pair of holes 15 and 16 are drilled through the elastomeric mold half from the inside of the groove 17 to the top side of the ridge 18 using a burr. The holes 15 and 16 are located at the medial and distal occlusal surfaces of the imprint in the mold of the area of restoration obtained from the model 10.

Figure 6:
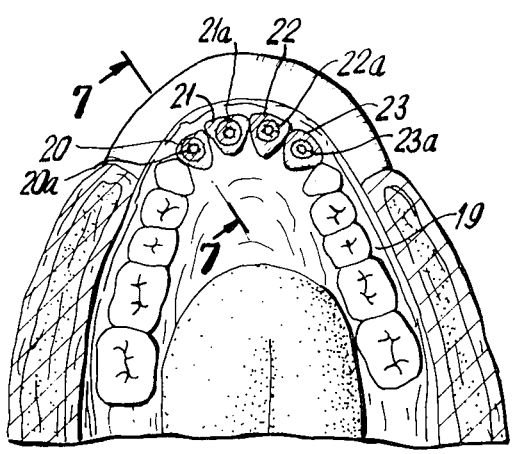
FIG. 6 is a plan view of the patient's jaw corresponding to the model, illustrating four of the front teeth after they have been prepared for receiving the prosthesis.
Figure 7:
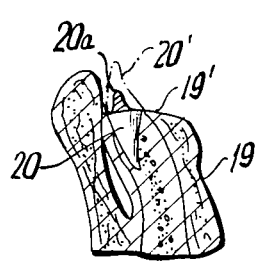
FIG. 7 is a cross sectional view taken on line 7—7 of FIG. 6 through one of the prepared teeth showing the outline of the original tooth in phantom and comparing it with the prepared tooth which has been cut down by grinding.

FIG. 6 shows the lower jaw 19 of a patient's mouth which has been prepared in a conventional manner to receive a bridge for the patient's front teeth 20, 21, 22 and 23. The teeth 21 and 22 are the teeth requiring a restoration and the teeth 20 and 23 and anchor teeth which have been cut down and will serve as anchors for the bridge. Each of the teeth in the restoration area have been cut down by grinding to provide stumps 20a, 21a, 22a, and 23a over which a temporary bridge will be molded in accordance with this invention and to which will be applied a permanent bridge after it has been prepared in a laboratory in the usual manner. Looking at FIG. 7, the original outline of the anchor tooth 20 which has been cut down to form the stump 20a is shown by the phantom line 20'.

Figure 8:
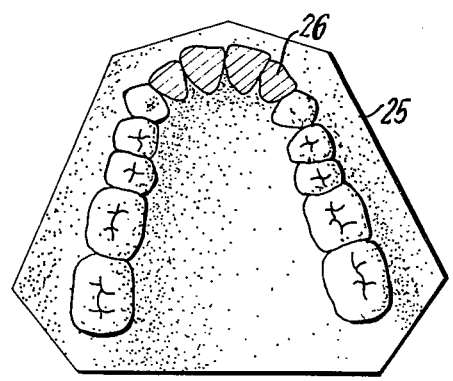
FIG. 8 is a top plan view of a positive model made of the patient's jaw after the teeth areas have bee prepared for receiving the prosthesis.

After the patient's teeth have been prepared in a manner as is usually required for a permanent restoration, a second positive model 25 is prepared, as shown in FIG. 8. This model can again be prepared in a conventional manner by first taking a negative impression of the jaw, then pouring a mix of hard setting dental model forming material such as dental stone, into the impression and allowing the mix to set, whereupon the impression is separated from the dental stone thus providing the positive model 25 with the patient's existing dentition. The model formed includes the tooth area which have been prepared such as teeth 26 which have been cut down as is shown by the shaded area.

Figure 9:
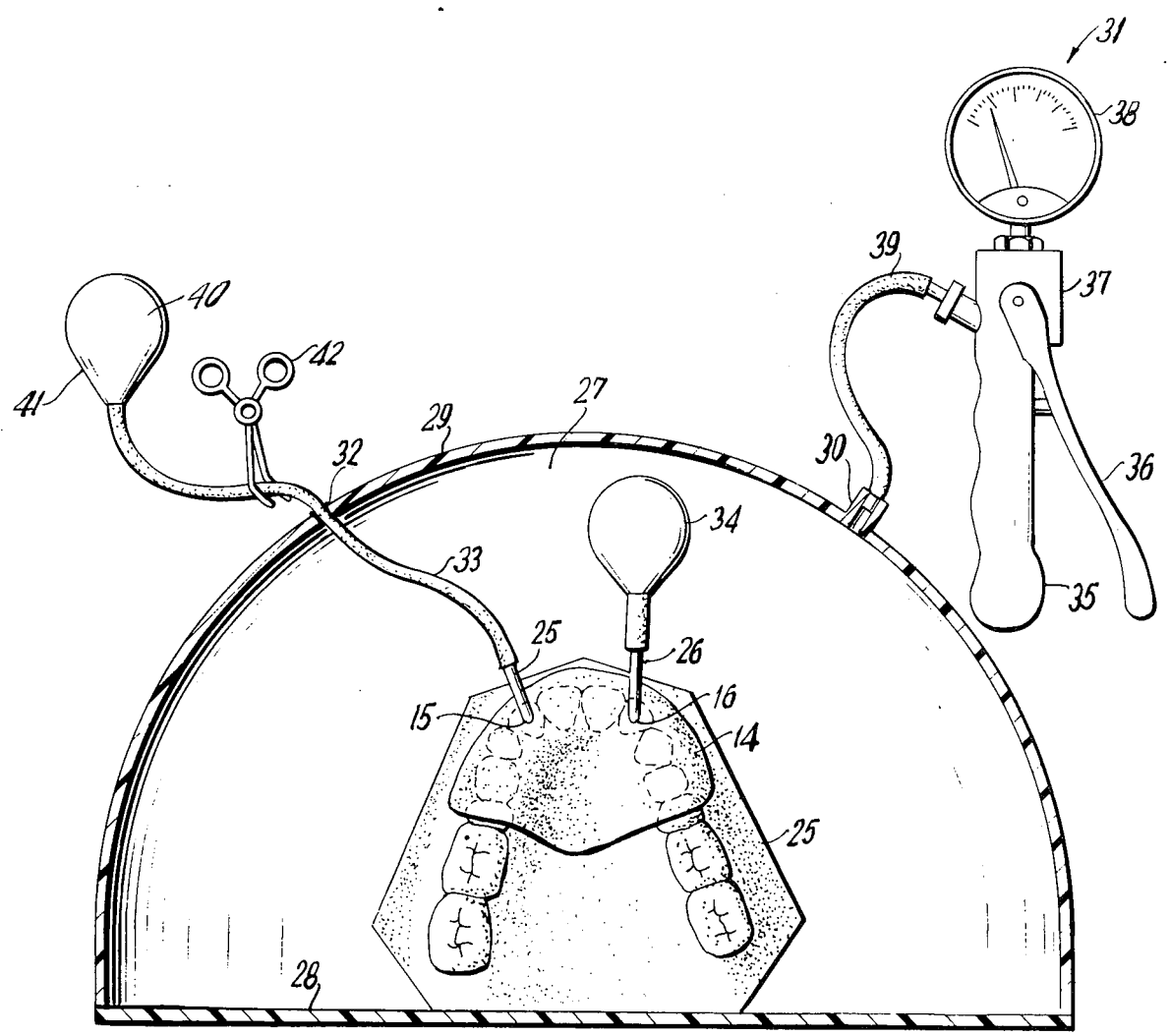
FIG. 9 shows the elastomeric mold assembled onto the positive model of FIG. 8 and placed within a vacuum chamber including the charging apparatus connected in place.

The elastomeric mold half 14 is then placed together with the positive stone model 25, as shown in FIG. 9, and properly aligned creating a mold cavity therebetween. The two halves are secured together by any type of securing means, such as a rubber band, etc. to preserve the proper alignment of the mold halves while the mold is being handled.

The assembled mold halves are then placed within a vacuum chamber 27 containing a base 28 and a outer wall 29 having an inlet fitting 30 through which a vacuum pump can be connected. The outer wall also includes a further opening 32.

Tubular fittings 25, 26 are placed in the holes 15 and 16 respectively, from the outside of the mold 14; one end of each tubular fitting being placed in the respective holes. To the other leg of the fitting 25 is connected a flexible inlet tube 33 of sufficient length to pass through the opening 32 in the wall 29 of the vacuum chamber. The tubular fitting 26 is connected to an overflow container 34, shown as a syringe barrel. The syringe barrel 34 is positioned within the vacuum chamber.

A vacuum pump 31 is provided with a handle 35 and an operating lever 36 which is operatively connected to a reciprocating piston (not shown) inside of the pump cylinder housing 37. A vacuum gauge 38 is mounted on the cylinder housing 37 and is operatively connected to the inlet side of the pump. A tube 39 interconnects the pump 31 to the fitting 30 in the wall of the vacuum chamber. While one type of vacuum pump is shown, any other type well known in the art could be utilized including a vacuum pump permanently connected to the vacuum chamber.

The end of the flexible tube 33 which passes through the opening 32 in the wall of the vacuum chamber is adapted to be inserted into a receptacle in which a supply of liquid resin forming material 40 is placed. As is shown, a syringe 41 is utilized, however an open receptacle could also be used for either of the syringes 34, 41 to function in the same manner as set forth below. A clamp 42, which may be a hemostat or other suitable hose clamp, is provided for clamping the hose 33 at a position exterior of the vacuum chamber. Instead of the hemostat, a person's fingers may be used as the clamp to close the inlet tube 33.

A mix 40 of tooth shaded, self-curing liquid acrylic resin of a type commonly used in dentistry is then mixed in the receptacle 41. Inlet tube 33 is then clamped with the hemostat 42 in between the vacuum chamber and the container 41. The vacuum pump is then actuated and the chamber is evacuated to provide a static vacuum therein. By way of example, a vacuum of about 3 inches of mercury read on the vacuum gauge would be sufficient. The clamp 42 of the inlet tubing is then released allowing the tube 33 to open whereupon the atmospheric pressure acting on the material in the container or on the syringe 41 pushes the liquid resin through the tube 33 into the mold cavity formed between the elastomeric mold and the stone model.

The liquid resin fills the mold cavity and continues until if flows into the reservoir 34 indicating that the mold is filled. The flow of material is then stopped by clamping the inlet tube 33. This prevents the acrylic from running back out of the tube 33 when the vacuum on the exhaust side of the mold is released.

The material may then be allowed to cure either under continued static vacuum pressure, or the vacuum can be released, depending upon what effect the vacuum will have on the material used. Once the mold cavity is filled, the molded material may then be processed by various procedures including heating, cooling, submerging, pressurizing, or any of the curing methods depending upon the curing procedure for the material being used. The process described is designed to fill the mold without any flash by using atmospheric or lower pressure.

Figure 10:
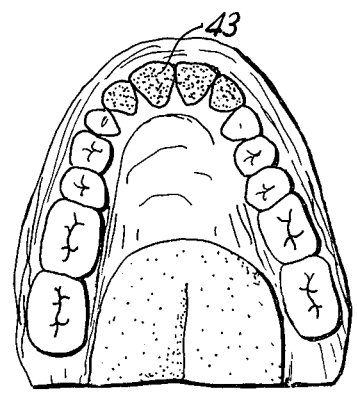
FIG. 10 is a plan view of the patient's jaw showing the restored front teeth.

Throughout this specification, the terms "prosthesis" and "restoration" have been used more or less interchangeably to mean any artificial device which replaces or restores missing teeth or missing portions of worn or broken teeth to the original contour of the teeth or to a corrected contour as determined by a dentist. The example of a temporary bridge for capping two broken front teeth is given for purpose of illustration only, of one form of prosthesis which may be made by the method of this invention. The temporary bridge 43 indicated by the stippled area in FIG. 10 is a one piece molded cap for the four front teeth 20–23 illustrated in FIG. 6. The contour of the individual teeth and the crevices between the individual teeth are precisely formed by the method and apparatus of this invention. By placing the mold cavity within a vacuum chamber and relying on the atmospheric pressure acting on the surface of the liquid resin in the supply vessel, such as the syringe 41, to push the liquid resin into the evacuated mold cavity, the mold cavity is completely filled with the liquid resin. Thus, voids in the prosthesis which would result from air entrapment are avoided.

While various types of elastomers may be used to form the elastomeric mold 14, one which has been found to be satisfactory is the dental silicone base impression material sold under the trademark JELCONE R by The L. D. Caulk Co. a Division of Dentiply International, Inc.

The prosthesis forming material may also be one of various self-curing synthesis resin materials used in dentistry. One such material comprises an acrylic resin forming liquid and powder sold under the trade name Trim by the Harry J. Bosworth Company. The liquid and powder are mixed in the container 41 to form a thin liquid mixture capable of flowing through the inlet tube 33 into the mold cavity as shown in FIG. 9 of the drawing. The invention is not limited to the use of acrylic type synthetic resins as other self-curing non-toxic resin materials adapted for use in forming dental restorations may be used.

Although the pair of holes drilled into the elastomeric mold 14 is shown at opposite ends of the mold cavities, it is also possible, although not as efficient, to place the pair of holes at the same end of the mold cavity.

There has been disclosed heretofore the best embodiments of the invention presently contemplated. However, it is to be understood that various changes and modifications may be made thereto without departing from the spirit of the invention.

What is claimed is:

1. A method for forming a dental prosthesis in situ, comprising: forming an elastomeric mold of a corrected model of tooth areas to be restored; performing tooth preparatory work in the tooth areas to be restored including the removal of portions thereof; forming a model of the tooth area prepared for restoration; making a pair of channels through the elastomeric mold at spaced apart locations therein; securing the elastomeric mold to the model to form an assembly including a mold cavity therein; placing the assembly in a vacuum chamber for pumping a vacuum inside of said chamber; connecting an overflow container within the vacuum chamber to one of the channels; connecting a source of liquid prosthesis forming material outside of the vacuum chamber to the other of the channels; closing the connection between said source of material and said assembly; pumping a vacuum inside of said chamber to a predetermined level, and opening the connection between the source of material and the assembly whereby atmospheric pressure acting on the liquid prosthesis forming the material pushes said liquid prosthesis forming material into the mold cavity.

2. A method as claimed in claim 1, wherein said step of forming an elastomeric mold further comprises the steps of: taking an impression of the patient's mouth and forming a model of the patient's dentition with a hard setting dental model forming material; correcting the model by filling in the areas of the teeth which are to be restored with model correcting material until the corrected areas conform to the desired size and shape of the restored teeth; applying a pliable and curable mold forming elastomeric material over the model, and curing the negative mold while it is still on the model.

3. A method as claimed in claim 1 further comprising the steps of: applying a tubular fitting in each of said pair of channels, said overflow container being connected to one of the fittings; and connecting a flexible inlet tube to the other one of said fittings, said source of liquid prosthesis being connected to said flexible inlet tube.

4. A method as claimed in claim 3, wherein said vacuum chamber includes an inlet port, and further comprising the step of passing the flexible inlet tube through the inlet port, and clamping the tube on the outside of the vacuum chamber.

5. A method as claimed in claim 1 further comprising the step of preparing a mix of self-curing acrylic liquid resin in a syringe, and connecting the syringe as the source of liquid prosthesis forming material.

6. A method as claimed in claim 1 further comprising the step of allowing the prosthesis forming material to cure within the mold cavity of the assembly, and then removing the prosthesis from the assembly.

7. A method as claimed in claim 1, wherein said predetermined vacuum is about 3 inches of Hg.

8. A method as claimed in claim 1, wherein said channels are proved at opposite ends of the mold cavity.

9. Apparatus for forming a dental prosthesis, comprising an elastomeric mold half which has been prepared over a first positive model of a patient's jaw requiring restoration, said mold half having an internal impression of a restoration desired, a second positive model of the patient's jaw including a cavity for receiving the prosthesis, means for joining said mold half and said second positive model together with said cavity therebetween to define an assembly, a chamber to receive said assembly therein, means for providing a vacuum within said chamber, overflow container means for connection to the elastomeric mold half in communication with said cavity and positioned within the chamber, a souce for containing a mix of self-curing liquid resin disposed outside said chamber, a flexible inlet conduit means for connection between the elastomeric mold half in communication with said cavity and said source in communication with said liquid resin, and means for opening and closing said inlet tube conduit means to control flow of said liquid resin through said inlet conduit means to said cavity in said assembly, whereby said overflow container means receives overflow amount of said liquid resin from said cavity.

10. An apparatus as claimed in claim 9, wherein at least one of said source for containing the resin and said overflow container includes a syringe means.

11. An apparatus as claimed in claim 9, wherein said second positive model is formed of hard setting dental stone material.

* * * * *